(12) United States Patent
Juhn et al.

(10) Patent No.: US 10,654,923 B2
(45) Date of Patent: May 19, 2020

(54) METHODS FOR TREATING MEDICAL CONDITIONS BY ANTI-TYPE 2 THERAPY

(71) Applicant: Mayo Foundation for Medical Education and Research, Rochester, MN (US)

(72) Inventors: Young J. Juhn, Rochester, MN (US); Hirohito Kita, Rochester, MN (US); Melissa R. Snyder, Rochester, MN (US); Jenna Corrinne Podjasek, Orland Park, IL (US); Chung Ii Wi, Rochester, MN (US); Euijung Ryu, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 187 days.

(21) Appl. No.: 15/387,324

(22) Filed: Dec. 21, 2016

(65) Prior Publication Data
US 2017/0183402 A1    Jun. 29, 2017

Related U.S. Application Data

(60) Provisional application No. 62/271,826, filed on Dec. 28, 2015.

(51) Int. Cl.
*C07K 16/24* (2006.01)
*G01N 33/68* (2006.01)

(52) U.S. Cl.
CPC .......... *C07K 16/241* (2013.01); *C07K 16/244* (2013.01); *C07K 16/247* (2013.01); *G01N 33/6863* (2013.01); *G01N 2333/54* (2013.01); *G01N 2333/5406* (2013.01); *G01N 2333/5409* (2013.01); *G01N 2333/5437* (2013.01); *G01N 2333/55* (2013.01); *G01N 2333/57* (2013.01); *G01N 2800/065* (2013.01); *G01N 2800/102* (2013.01); *G01N 2800/122* (2013.01)

(58) Field of Classification Search
None
See application file for complete search history.

(56) References Cited

U.S. PATENT DOCUMENTS

| | | | |
|---|---|---|---|
| 7,514,232 B2 | 4/2009 | Maino et al. | |
| 2012/0015824 A1 | 1/2012 | Love et al. | |
| 2013/0034844 A1 | 2/2013 | Boyle et al. | |

FOREIGN PATENT DOCUMENTS

| | | |
|---|---|---|
| EP | 1389129 | 2/2004 |
| WO | WO 2002074328 | 9/2002 |
| WO | WO 2004042396 | 5/2004 |
| WO | WO 2013087917 | 6/2013 |

OTHER PUBLICATIONS

Kang et al. Airway cytokine responses to acute and repeated stress in a murine model of allergic asthma. Biol. Psychol. 84, 66-73, 2010. (Year: 2010).*
Catley et al. (Monoclonal antibodies for the treatment of asthma. Pharmacol. Therapeut. 132, 333-351, 2011. (Year: 2011).*
"QuantiFERON" Sep. 10, 2017, Retrieved on Oct. 19, 2017, Retrieved from the Internet: URL: https://en.wikipedia.org/wiki/QuantiFERON, 6 pages.
Brown et al. "A recombinant Sendai virus is controlled by CD4+ effector T cells responding to a secreted human immunodeficiency virus type 1 envelope glycoprotein," *J Virol.*, 81(22):12535-12542, Nov. 2007.
Chatzigeorgiou et al., "The pattern of inflammatory/anti-inflammatory cytokines and chemokines in type 1 diabetic patients over time," *Ann Med.*, 42(6):426-438, Sep. 2010.
Corren et al., "Lebrikizumab treatment in adults with asthma," *N Engl J Med.*, 365(12):1088-1098, 2011.
Damsgaard et al., "Whole-blood culture is a valid low-cost method to measure monocytic cytokines—a comparison of cytokine production in cultures of human whole-blood, mononuclear cells and monocytes," *J Immunol Methods.*, 340(2):95-101, Jan. 30, 2009.
De Groote et al., "Direct stimulation of cytokines (IL-1 beta, TNF-alpha, IL-6, IL-2, IFN-gamma and GM-CSF) in whole blood. I. Comparison with isolated PBMC stimulation," *Cytokine*, 4(3):239-248, May 1992.
Duramad et al., "Expression of Th1/Th2 cytokines in human blood after in vitro treatment with chlorpyrifos, and its metabolites, in combination with endotoxin LPS and allergen Der p1," *J Appl Toxicol.*, 26(5): 458-465, Sep.-Oct. 2006.
Farrell et al., "A rapid flow cytometric assay to detect CD4+ and CD8+ T-helper (Th) 0, Th1 and Th2 cells in whole blood and its application to study cytokine levels in atopic dermatitis before and after cyclosporin therapy," *Br J Dermatol.*, 144(1): 24-33, Jan. 2001.
Feldmann and Maini "Anti-TNFα therapy of rheumatoid arthritis: What have we learned?" Annu Rev Immunol., 19(1):163-196, 2001.
Gomez-Tourino et al., "Galectin-1 synthesis in type 1 diabetes by different immune cell types: reduced synthesis by monocytes and Th1 cells," *Cell Immunol.*, 271(2):319-328, 2011.
Haldar et al., "Mepolizumab and exacerbations of refractory eosinophilic asthma," *N Engl J Med.*, 360(10):973-984, 2009.
Hanania et al., "Lebrikizumab in moderate-to-severe asthma: pooled data from two randomised placebo-controlled studies," *Thorax.*, 70(8):748-756, Aug. 2015.
Heaton et al., "Staphylococcal enterotoxin induced IL-5 stimulation as a cofactor in the pathogenesis of atopic disease: the hygiene hypothesis in reverse?" *Allergy.*, 58(3):252-256, Mar. 2003.
Hermann et al., "A model of human whole blood lymphokine release for in vitro and ex vivo use," *J Immunol Methods.*, 275(1-2):69-79, Apr. 1, 2003.

(Continued)

*Primary Examiner* — Elly-Gerald Stoica
(74) *Attorney, Agent, or Firm* — Fish & Richardson P.C.

(57) ABSTRACT

This document provided methods and materials involved in treating medical conditions. For example, methods and materials for using anti-Interleukin 4, anti-Interleukin 5, and/or anti-Interleukin 13 antibodies to treat asthma in a mammal identified as having a Th2 immune response using a whole blood cell-based cytokine whole blood cell-based cytokine assay are provided.

3 Claims, 2 Drawing Sheets

(56) References Cited

OTHER PUBLICATIONS

Hollams et al., "Th2-associated immunity to bacteria in teenagers and susceptibility to asthma," *Eur Respir J.*, 36(3):509-516, Sep. 2010.
Jung et al., "Influence of asthma status on serotype-specific pneumococcal antibody levels," *Postgrad Med.*, 122(5):116-24, Sep. 2010.
Larsen et al., "Complex cytokine responses to hepatitis B surface antigen and tetanus toxoid in responders, nonresponders and subjects naive to hepatitis B surface antigen," *Vaccine.*, 18(26):3021-30, Jul. 2000.
Moss et al., "Th1/Th2 cells in inflammatory disease states: therapeutic implications," *Expert Opin Biol Ther.*, 4(12):1887-1896, 2004.
Nair et al., "Mepolizumab for prednisone-dependent asthma with sputum eosinophilia," *N Engl J Med.*, 360(10):985-993, 2009.
Ng et al., "Cellular immune responses to ovalbumin and house dust mite in egg-allergic children," *Allergy.*, 57(3): 207-214, Mar. 2002.
Ortega et al., "Mepolizumab treatment in patients with severe eosinophilic asthma," *N Engl J Med.*, 371(13):1198-1207, Sep. 25, 2014.
Pavord et al., "Mepolizumab for severe eosinophilic asthma (DREAM): a multicentre, double-blind, placebo-controlled trial," *Lancet.*, 380(9842):651-659, Aug. 18, 2012.
Podjasek et al., "Development and Initial Testing of Whole Blood Cell Stimulation Assay to Determine Th1 Vs. Th2 Immune Profiles," *J Allergy Clin Immunol*, 135(2): AB176, Feb. 2, 2015.
Podjasek et al., "The Fact score in predicting pneumococcal antibody levels in asthmatics," *J Asthma.*, 22:1-6, Oct. 2014.
Rutgeerts et al "Infliximab for induction and maintenance therapy for ulcerative colitis," *N Engl J Med.*, 353(23):2462-2476, Dec. 8, 2005.
Schmidt-Weber., "Anti-IL-4 as a new strategy in allergy," *Chem Immunol Allergy.*, 96:120-125, 2012.
Schultz-Thater et al., "Whole blood assessment of antigen specific cellular immune response by real time quantitative PCR: a versatile monitoring and discovery tool," *J Transl Med.*, 6:58, Oct. 16, 2008.
Smart and Kemp., "Increased Th1 and Th2 allergen-induced cytokine responses in children with atopic disease," *Clin Exp Allergy.*, 32(5):796-802, May 2002.
Swaak et al., "Cytokine production in whole blood cell cultures of patients with rheumatoid arthritis," *Ann Rheum Dis.*, 56(11):693-695, Nov. 1997.
Taylor and Pavord, "Biomarkers in the assessment and management of airways diseases," *Postgrad Med J.*, 84(998):628-634; quiz 633, Dec. 2008.
Thurm et al., "Measurement of cytokine production using whole blood," *Curr Protoc Immunol.*, Chapter 7:Unit 7.18B, May 2005.
Wenzel et al., "Dupilumab in Persistent Asthma with Elevated Eosinophil Levels," *N Engl J Med.*, 368(26):2455-2466, Jun. 27, 2013.
Williams et al., "The contribution of allergen-specific IgG to the development of th2-mediated airway inflammation," *J Allergy (Cairo).*, 2012:236075, 2012.
Wilson et al., "A convenient human whole blood culture system for studying the regulation of tumour necrosis factor release by bacterial lipopolysaccharide," *J Immunol Methods.*, 139(2):233-240, Jun. 3, 1991.
Yaqub et al., "A human whole blood model of LPS-mediated suppression of T cell activation," *Med Sci Monit.*, 9(3):BR120-6, Mar. 2003.
Brightling et al., "TH2 cytokine expression in bronchoalveolar lavage fluid T lymphocytes and bronchial submucosa is a feature of asthma and eosinophilic bronchitis," Journal of Allergy and Clinical Immunology, 110(6):899-905, Dec. 2002.
Hansen et al., "Bronchoalveolar lavage fluid cytokine, cytology and IgE allergen in horses with equine asthma," J. Immunol., 177(9):6460-70, Nov. 2006.
Hosoki et al., "Analysis of a Panel of 48 Cytokines in BAL Fluids Specifically Identifies IL-8 Levels as the Only Cytokine that Distinguishes Controlled Asthma from Uncontrolled Asthma, and Correlates Inversely with FEV1," PLoS One, 10(5): e0126035, May 2015.
Meyts et al., "IL-12 Contributes to Allergen-Induced Airway Inflammation in Experimental Asthma," J. Immunol., 177(9):6460-6470, Nov. 2006.
Robinson et al., "Predominant TH2-like Bronchoalveolar T-Lymphocyte Population in Atopic Asthma," N. Engl. J. Med., 326:298-304, Jan. 1992.
Walker et al., "Allergic and nonallergic asthmatics have distinct patterns of T-cell activation and cytokine production in peripheral blood and bronchoalveolar lavage," American Review of Respiratory Disease, 146(1):109-15, Jul. 1992.

\* cited by examiner

FIG. 2

METHODS FOR TREATING MEDICAL CONDITIONS BY ANTI-TYPE 2 THERAPY

CROSS-REFERENCE TO RELATED APPLICATIONS

This application claims the benefit of U.S. Provisional Application Ser. No. 62/271,826, filed Dec. 28, 2015. The disclosure of the prior application is considered part of (and is incorporated by reference in) the disclosure of this application.

BACKGROUND

1. Technical Field

This document relates to methods and materials involved in treating medical conditions. For example, this document provides methods and materials for using anti-interleukin 4 (anti-IL4), anti-interleukin 5 (anti-IL5), and/or anti-interleukin 13 (anti-IL13) antibodies to treat asthma in a mammal identified as having a type 2 (or T helper 2 (Th2) (vs. type 1 or non-Th2) immune response using a whole blood cell-based cytokine assay.

2. Background Information

T helper 2 (Th2) and T helper 1 (Th1) cells in humans play a role for normal immune responses to various antigens including microbial organisms and are a major source of type 2 cytokines and immune responses and type 1 cytokines and immune responses, respectively. Th2 and Th1 cells have a reciprocal inhibitory relationship to each other, and an imbalance of these immune functions can potentially result in aberrant immune responses leading to allergic disorders such as asthma or pro-inflammatory conditions such as rheumatoid arthritis. For example, anti-type 2 cytokine therapy including anti-interleukin 4, anti-interleukin 5, and/ or anti-interleukin 13 antibodies has shown clinical efficacy for treating type 2 predominant conditions (e.g., severe asthma). The FDA recently approved anti-interleukin 5 (anti-IL5; mepolizumab) for treating patients with severe asthma.

SUMMARY

This document provides methods and materials for treating medical conditions such as those having either a predominant type 2 immune response or a predominant type 1 immune response. For example, this document provides methods and materials for identifying patients with type 2 predominant conditions (e.g., severe asthma), who can be treated with anti-IL5 antibodies (e.g., mepolizumab) or other anti-type 2 cytokine antibodies (e.g., anti-IL4 or anti-IL13 antibodies), by using a whole blood cell-based cytokine assay (e.g., Interleukin 5/Interleukin 2, Interleukin 4/Interleukin 2, and/or Interleukin 13/Interleukin 2 ratios). In some cases, the responses to the therapy can be monitored using a whole blood cell-based cytokine assay (e.g., Interleukin 5/Interleukin 2, Interleukin 4/Interleukin 2, and/or Interleukin 13/Interleukin 2 ratios). This document also provides methods and materials for (a) identifying a mammal with a medical condition that has a predominant type 2 immune response (e.g., asthma) using a whole blood cell-based cytokine assay and (b) administering an anti-type 2 cytokine therapy to the identified mammal to treat such a medical condition and/or to monitor responses to therapy. In addition, this document provides methods and materials for (a) identifying a mammal with a medical condition that has a predominant type 1 immune response (e.g., rheumatoid arthritis) using a whole blood cell-based cytokine assay and (b) administering an anti-type 1 cytokine therapy to the identified mammal to treat such a medical condition and/or to monitor responses to therapy. As described herein, a mammal having a medical condition with a predominant type 2 immune response (e.g., asthma) or a predominant type 1 immune response (e.g., rheumatoid arthritis) can be rapidly and reliably identified and/or monitored using a whole blood cell-based cytokine assay. Those mammals identified as having a medical condition with a predominant type 2 immune response (e.g., asthma) as described herein can be treated using one or more anti-type 2 cytokine therapies (e.g., an anti-Interleukin 5 antibody such as mepolizumab) and/or monitored for responses to therapy, while those mammals identified as having a medical condition with a predominant type 1 immune response (e.g., rheumatoid arthritis) as described herein can be treated using one or more anti-type 1 cytokine therapies (e.g., an anti-Tumor Necrosis Factor-α antibody such as infliximab) and/ or monitored for responses to therapy.

In general, one aspect of this document features a method for treating a medical condition in a mammal. The method comprises, or consists essentially of, (a) identifying the mammal as having a medical condition having a predominant type 2 immune response using a whole blood cell-based cytokine assay, and (b) administering an anti-type 2 therapy to the mammal under conditions wherein the severity of the medical condition within the mammal is reduced. The mammal can be a human. The medical condition can be asthma. The whole blood cell-based cytokine assay can comprise (i) culturing a whole blood sample with a stimulant to obtain a culture supernatant, and (ii) determining the level of two or more cytokines within the culture supernatant. The whole blood sample can be undiluted, unfrozen and heparinized. The stimulant can be Staphylococcal enterotoxin B (SEB). The two or more cytokines can be selected from the group consisting of Interleukin 4, Interleukin 5, Interleukin 13, Interleukin 2, Interferon-γ, and Tumor Necrosis Factor-α. The method can comprise calculating an Interleukin 5 to Interleukin 2 ratio. The anti-type 2 cytokine therapy can be an anti-Interleukin 4 antibody therapy, an anti-Interleukin 5 antibody therapy, or an anti-Interleukin 13 antibody therapy. The method can comprise calculating an Interleukin 4 to Interleukin 2 ratio, wherein the mammal is identified as having the medical condition having the predominant type 2 immune response based on the Interleukin 4 to Interleukin 2 ratio being greater than 40.0.

In another aspect, this document features a method for treating a medical condition in a mammal. The method comprises, or consists essentially of, (a) identifying the mammal as having a medical condition having a predominant type 1 immune response using a whole blood cell-based cytokine assay, and (b) administering an anti-type 1 cytokine therapy to the mammal under conditions wherein the severity of the medical condition within the mammal is reduced. The mammal can be a human. The medical condition can be inflammatory bowel disease or rheumatoid arthritis. The whole blood cell-based cytokine assay can comprise (i) culturing a whole blood sample with a stimulant to obtain a culture supernatant, and (ii) determining the level of two or more cytokines within the culture supernatant. The whole blood sample can be undiluted and heparinized. The stimulant can be Staphylococcal enterotoxin B (SEB). The two or more cytokines can be selected from the group consisting of Interleukin 4, Interleukin 5, Interleukin 13, Interleukin 2, Interferon-γ, and Tumor Necrosis Factor-α. The method can comprise calculating an Interleukin 5 to Interleukin 2 ratio. The anti-type 1 therapy can be an anti-Tumor Necrosis Factor-α antibody therapy.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

This document provides methods and materials for treating a mammal identified as having a medical condition having either a predominant type 2 immune response (e.g., asthma) or a predominant type 1 immune response (e.g., rheumatoid arthritis) using a whole blood cell-based cytokine assay. Any appropriate mammal can be identified, treated, and/or monitored as described herein. For example, humans and other primates such as monkeys can be identified as having a medical condition having either a predominant type 2 immune response or a predominant type 1 immune response using a whole blood cell-based cytokine assay and treated as described herein. In some cases, dogs, cats, horses, bovine species, pigs, sheep, mice, and rats can be identified and treated as described herein.

A whole blood cell-based cytokine assay described herein can be used to assess if any appropriate medical condition has either a predominant type 2 immune response or a predominant type 1 immune response. For example, a whole blood cell-based cytokine assay described herein can be used to determine if a mammal has a medical condition having a predominant type 2 immune response. Examples of medical conditions having a predominant type 2 immune response that can be identified using a whole blood cell-based cytokine assay described herein include, without limitation, asthma, atopic dermatitis (e.g., eczema), and allergic rhinitis (e.g., hay fever). In some cases, a whole blood cell-based cytokine assay described herein can be used to determine if a mammal has a medical condition having a predominant type 1 immune response. Examples of medical conditions having a predominant type 1 immune response that can be identified using a whole blood cell-based cytokine assay described herein include, without limitation, inflammatory bowel disease, Crohn's disease, ulcerative colitis, rheumatoid arthritis, and type I diabetes.

In general, a whole blood cell-based cytokine assay described herein includes (a) culturing unfrozen whole blood sample in the presence of one or more stimulants (e.g., one, two, three, four, five, six, or more stimulants) for a period of time (e.g., from about 18 to about 30 hours or about 24 hours) to obtain a culture supernatant and (b) determining the level of one or more cytokines (e.g., one, two, three, four, five, six, or more cytokines) present in the culture supernatant. For example, about 250 μL to 750 μL (e.g., about 500 μL) of whole blood (e.g., heparinized whole blood obtained from a human to be assessed) can be cultured in the presence of one or more stimulants (e.g., Staphylococcal enterotoxin B) for a period of time (e.g., 24 hours) to obtain a culture supernatant. Examples of stimulants that can be used in a whole blood cell-based cytokine assay described herein include, without limitation, concanavalin A, tetanus toxoid, house dust mite, lipopolysaccharide, Staphylococcal enterotoxin B (SEB), and phorbol 12-myristate 13-acetate (PMA)-ionomycin. For example, whole blood can be cultured in the presence of Staphylococcal enterotoxin B for a period of time (e.g., from about 18 to about 30 hours, or about 24 hours) to obtain a culture supernatant. When using about 250 μL to 750 μL (e.g., about 500 μL) of undiluted unfrozen whole blood (e.g., undiluted heparinized whole blood obtained from a human to be assessed), the amount of concanavalin A as stimulant (e.g., as the sole stimulant) can be about 5 μg/mL, the amount of tetanus toxoid as stimulant (e.g., as the sole stimulant) can be about 1 μg/mL, the amount of house dust mite as stimulant (e.g., as the sole stimulant) can be about 25 μg/mL, the amount of lipopolysaccharide as stimulant (e.g., as the sole stimulant) can be about 1 μg/mL, the amount of Staphylococcal enterotoxin B as stimulant (e.g., as the sole stimulant) can be about 1 μg/mL or less, or the amount of PMA-ionomycin (e.g., as the sole stimulant) can be about 50 ng/mL of PMA and 1 μg/mL of ionomycin.

The whole blood can be cultured in the presence of one or more stimulants for any appropriate period of time to obtain a culture supernatant. For example, the whole blood cells can be cultured in the presence of one or more stimulants for about 24 hours (e.g., from about 18 hours to about 72 hours, from about 18 hours to about 48 hours, from about 18 hours to about 36 hours, from about 18 hours to about 30 hours, or from about 20 hours to about 28 hours).

After culturing, the culture supernatant can be obtained and assessed to determine the level of one or more cytokines (e.g., one or more type 2 cytokines, one or more type 1 cytokines, one or more growth factors for T-cells and/or one or more T helper 17 cytokines). Examples of type 2 cytokines that can be assessed include, without limitation, Interleukin 4, Interleukin 5, and Interleukin 13. Examples of type 1 cytokines that can be assessed include, without limitation, IFN-γ, TNF-α, and Interleukin 12. Examples of a growth factor for T cells that can be assessed include, without limitation, Interleukin 2. Examples of T helper 17 cytokines that can be assessed include, without limitation, Interleukin 17. Any appropriate immune assay method can be used to determine cytokine levels within a culture supernatant. For example, ELISA (Enzyme Linked Immunosorbent Assay) techniques (e.g., multiplex ELISA techniques) or Bio-Rad Luminex assay or multiplex chemiluminescent chip assay can be used to determine the level of Interleukin 4, Interleukin 5, Interleukin 13, Interferon-γ, Tumor Necrosis Factor-α, Interleukin 2, and/or Interleukin 17 present within a culture supernatant.

The determined cytokine levels within a culture supernatant can be used to determine if the mammal has a medical condition having a predominant type 2 immune response or if the mammal has a medical condition having a predominant type 1 immune response. For example, the presence of elevated levels of type 2 cytokines and the presence of reduced levels of type 1 cytokines or a growth factor for T cells can indicate that the mammal has a medical condition having a predominant type 2 immune response, while the presence of elevated levels of type 1 cytokines and the presence of reduced levels of type 2 or a growth factor for T cells cytokines can indicate that the mammal has a medical condition having a predominant type 1 immune response. In some cases, ratios of different cytokines (e.g., Interleukin 5 to Interleukin 2, Interleukin 4 to Interleukin 2, Interleukin 13 to Interleukin 2, Interferon-γ to Interleukin 2, or Tumor Necrosis Factor-α to Interleukin 2 (or vice versa)) can be used to assess if the mammal has a medical condition having a predominant type 2 immune response or a medical condition having a predominant type 1 immune response. For example, a ratio of [(Interleukin 5)+10)] to log-transformed [(Interleukin 2)+10] greater than about 0.59 can indicate that the mammal has a medical condition having a predominant type 2 immune response such as asthma (sensitivity=0.9, specificity=0.9, and area under the curve=0.91). According to this cut-off value, the normal range for healthy individuals can be 0.49-0.58.

In some cases, a ratio of [(Interleukin 4)+10)] to log-transformed [(Interleukin 2)+10] greater than about 0.28 can indicate that the mammal has a medical condition having a predominant type 2 immune response such as asthma (sensitivity=0.8, specificity=0.8, and area under the curve=0.89). According to this cut-off value, the normal range for healthy individuals can be 0.26-0.28. Both ratios of Interleukin 4 to Interleukin 2 and Interleukin 5 to Interleukin 2 can be complementary in determining predominant type 2 immune responses in the mammal as each ratio assesses a different effector (IgE vs. eosinophils) of type 2 inflammation (Interleukin 4 to Interleukin 2 ratio measures IgE production and Interleukin 5 to Interleukin 2 ratio detects increase of eosinophils).

In some cases, a mammal can be identified as having a severe medical condition due to a predominant type 2 immune response (e.g., severe asthma) using a whole blood cell-based cytokine assay as described herein. For example, a ratio of log-transformed [(Interleukin 5)+10] to log-transformed [(Interleukin 2)+10] greater than about 0.64 can indicate that the mammal has a severe medical condition due to a predominant type 2 immune response such as severe asthma (sensitivity=1.0, specificity=0.75, and area under the curve=0.81) among those with asthma. In some cases, a ratio of log-transformed [(Interleukin 4)+10] to log-transformed [(Interleukin 2)+10] greater than about 0.40 can indicate that the mammal has a severe medical condition due to a predominant type 2 immune response such as severe asthma (sensitivity=1.0, specificity=0.78, and area under the curve=0.86) among those with asthma. In some cases, if a mammal with this severe condition (e.g., severe asthma) has not responded to traditional therapies (e.g., combination therapies for asthma), that mammal can be administered one or more anti-type 2 cytokine therapies (e.g., one, two, three, four, five, six, or more anti-type 2 cytokine therapies) to treat that medical condition.

Examples of anti-type 2 cytokine therapies that can be used to treat a mammal identified as having a medical condition having a predominant type 2 immune response and/or to monitor responses to therapy via a whole blood cell-based cytokine assay as described herein include, without limitation, anti-Interleukin 4 antibody therapies, anti-Interleukin 5 antibody therapies, and/or anti-Interleukin 13 antibody therapies. Examples of anti-Interleukin 4 antibody therapies include, without limitation, treatments with dupilumab. Examples of anti-Interleukin 5 antibody therapies include, without limitation, treatments with mepolizumab, reslizumab, and/or anrukinzumab. Examples of anti-Interleukin 13 antibody therapies include, without limitation, treatments with lebrikizumab. In some cases, ratios of Interleukin 4 to Interleukin 2 and Interleukin 5 to Interleukin 2 can be used to guide in choosing which anti-type 2 cytokine therapy (e.g., anti-Interleukin 4 vs. anti-Interleukin 5 antibody therapy) is suitable.

In some cases, after a mammal is identified as having a medical condition having a predominant type 1 immune response (e.g., rheumatoid arthritis), that mammal can be administered a therapy such as a therapy involving administration of methotrexate, systemic corticosteroids, and/or azathioprine and/or an anti-type 1 cytokine therapies (e.g., one, two, three, four, five, six, or more anti-type 1 cytokine therapies) to treat that medical condition. Examples of anti-type 1 cytokine therapies that can be used to treat a mammal identified as having a medical condition having a predominant type 1 immune response and/or to monitor responses to therapy using a whole blood cell-based cytokine assay as described herein include, without limitation, anti-Tumor Necrosis Factor-α antibody therapies and anti-Interferon-γ antibody therapies. Examples of anti-Tumor Necrosis Factor-α therapies include, without limitation, treatment with infliximab, etanercept, adalimumab, golimumab, and/or certolizumab. Examples of anti-Interferon-γ antibody therapies include, without limitation, treatment with fontolizumab.

In some cases, a mammal identified as having inflammatory bowel disease or rheumatoid arthritis having a predominant type 1 immune response using a whole blood cell-based cytokine assay as described herein can be administered an anti-Tumor Necrosis Factor-α antibody therapy to treat that inflammatory bowel disease or rheumatoid arthritis and/or to monitor responses to therapy.

While a mammal identified as asthma having a predominant type 2 immune response is being treated using a therapy such as an anti-type 2 cytokine therapy, often it is uncertain when these therapies can be discontinued. In some cases, a mammal that is being treated using such a therapy can be assessed and/or monitored for when such therapy can be modified using a whole blood cell-based cytokine assay as described herein.

While a mammal identified as having inflammatory bowel disease or rheumatoid arthritis having a predominant type 1 immune response is being treated using a therapy such as an anti-type 1 cytokine therapy, often it is uncertain when the therapy can be discontinued. In some cases, a mammal that is being treated using such a therapy can be assessed and/or monitored for when such therapy can be modified using a whole blood cell-based cytokine assay as described herein.

In some cases, one or more anti-type 2 cytokine therapies (or one or more anti-type 1 cytokine therapies) can be administered to a mammal once or multiple times over a period of time ranging from days to weeks. In some cases, one or more anti-type 2 cytokine therapies (or one or more anti-Type 1 cytokine therapies) can be formulated into a pharmaceutically acceptable composition for administration to a mammal having a medical condition identified as described herein. For example, a therapeutically effective amount of an anti-Interleukin 5 antibody (e.g., mepolizumab) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more anti-type 2 cytokine therapies (or one or more anti-type 1 cytokine therapies) can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more anti-type 2 cytokine therapies (or one or more anti-type 1 cytokine therapies) can be administered locally or systemically. In some cases, a composition provided herein can be administered systemically, locally (e.g., joint), orally, or by injection to a mammal (e.g., a human).

Effective doses can vary depending on the severity of the medical condition being treated, the route of administration, the age and general health condition of the subject, excipient usage, the possibility of co-usage with other therapeutic treatments such as use of other agents, and the judgment of the treating physician.

An effective amount of a composition containing one or more anti-type 2 cytokine therapies (or one or more anti-type 1 cytokine therapies) can be any amount that reduces the severity of the medical condition being treated within the mammal without producing significant toxicity to the mammal. For example, an effective amount of an anti-Interleukin-5 antibody such as mepolizumab can be about 100 mg subcutaneously administered every 4 weeks for 32 weeks.

If a particular mammal fails to respond to a particular amount, then the amount of the one or more anti-type 2 cytokine therapies (or the one or more anti-Th1 cytokine therapies) can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., asthma) may require an increase or decrease in the actual effective amount administered.

The frequency of administration of one or more anti-type 2 cytokine therapies (or one or more anti-type 1 cytokine therapies) can be any amount that reduces the severity of the medical condition being treated within the mammal without producing significant toxicity to the mammal. For example, the frequency of administration of one or more anti-type 2 cytokine therapies (or one or more anti-type 1 cytokine therapies) can be from about two to three times a week to about two to about three times a month. The frequency of administration of one or more anti-type 2 cytokine therapies (or one or more anti-type 1 cytokine therapies) can remain constant or can be variable during the duration of treatment. A course of treatment with a composition containing anti-type 2 cytokine therapies can include rest periods and be well spread out. For example, a composition containing anti-type 2 cytokine therapies (e.g., treatment with an anti-Interleukin 5 antibody such as mepolizumab) can be administered once every 4 weeks and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., asthma) may require an increase or decrease in administration frequency.

An effective duration for administering a composition containing one or more anti-type 2 cytokine therapies (e.g., treatment with an anti-Interleukin 5 antibody such as mepolizumab) (or one or more anti-type 1 cytokine therapies) can be any duration (e.g., about 32 weeks) that reduces the severity of the medical condition being treated within the mammal without producing significant toxicity to the mammal. In some cases, the effective duration can vary from several days to several weeks, months, or years. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and/or the severity of one or more symptoms related to the medical condition being treated (e.g., asthma) can be monitored. Any appropriate method can be used to determine whether or not the severity of the medical condition being treated is reduced. For example, lung assessment techniques can be used to assess the severity of asthma within a mammal.

The invention will be further described in the following examples, which do not limit the scope of the invention described in the claims.

EXAMPLES

Example 1—Whole Blood Cell-Based Cytokine Assay to Determine Predominant Type 2 (Vs. Non-Type 2) Immune Response as an Alternative to Peripheral Blood Mononuclear Cell-Based Cytokine Assay Subjects The first group of subjects included ten individuals with asthma that met pre-determined definite criteria for asthma (Table 1). The second group included ten healthy individuals as controls without asthma (Table 1). Potential control subjects were excluded if they had any history of other allergic disorders in the form of asthma, allergic rhinitis, and/or eczema.

TABLE 1

Baseline patient characteristics.

| Characteristic | Individuals without asthma (n = 10) | Individuals with asthma (n = 10) | P-value |
|---|---|---|---|
| Age in years, median (IQR)* | 10.0 (8.2, 11.8) | 10.3 (9.3, 11.8) | 0.52 |
| Male gender, n (%) | 5 | 5 | — |
| Caucasian, n (%) | 9 (90) | 6 (60) | 0.30 |
| Allergic rhinitis, n (%) | 0 | 8 (80) | <0.01 |
| Atopic dermatitis, n (%) | 0 | 5 (50) | 0.03 |
| Total IgE, median (IQR)* | 30.2 (17.7, 51.1) | 89.6 (48.9, 868.8) | 0.06 |
| Atopic/sensitization status, n (%)** | 3 (30) | 8 (80) | 0.07 |
| Immunoglobulins, median (IQR)* | | | |
| IgG | 984.5 (869, 1142.5) | 982.5 (782.3, 1075) | 0.57 |
| IgA | 126 (76.8, 169.8) | 152 (102, 205.6) | 0.36 |
| IgM | 121.5 (79.5, 142.5) | 95 (77.5, 115) | 0.30 |

*Interquartile range;
**Determined by positive serum-specific (>35 kU/L) serum-specific IgE levels to cat dander, short ragweed, Timothy grass, Elm tree, Oak tree, house dust mite (*Dermatophagoides farina*), and *Alternaria Tenuis*

Peripheral Blood Mononuclear Cells (PBMC) cytokine assays 50 mL of heparinized blood was collected from each of the ten subjects with asthma and from each of the ten age- and gender-matched healthy controls. The peripheral blood mononuclear cells (PBMC) were isolated and cultured with (a) media alone (negative control), (b) concanavalin A (5 µg/mL; positive control), (c) tetanus toxoid (1 µg/mL), (d) house dust mite (25 µg/mL), (e) lipopolysaccharide (1 µg/mL), or (f) Staphylococcal enterotoxin B (SEB; 1 µg/mL). The supernatant was collected on days 1, 4, and 7, centrifuged, and stored at −20° C. Cytokine (Interleukin 4, Interleukin 5, Interleukin 13, Interleukin 2, Interferon-γ, and Interleukin 17) levels were measured by multiplex ELISA (Enzyme Linked Immunosorbent Assay) for the samples collected on days 1, 4, and 7.

Whole Blood Cytokine Assay

Whole blood cell-based cytokine assays were tested to address the significant limitations of peripheral blood mononuclear cells-based (PBMC) cytokine assays, which include longer turnaround time (from 3 to 7 days), labor intensive (e.g., peripheral blood mononuclear cells, PBMC isolation from whole blood requires significant effort), and costlier (e.g., half-day effort of trained technicians) than whole blood cell-based cytokine assays (24 hour turn-around time and neither isolation procedures nor the corresponding effort from lab technician is required). 10 mL of whole blood was collected from each of the ten subjects with asthma and from each of the ten age- and gender-matched healthy controls. Within 4 hours, 500 µl of heparinized whole blood was cultured undiluted in the presence of (a) media alone (negative control), (b) concanavalin A (5 µg/mL; positive control), (c) tetanus toxoid (1 µg/mL), (d) house dust mite (25 µg/mL), (e) lipopolysaccharide (1 µg/mL), or (f) Staphylococcal enterotoxin B (SEB; 1 µg/mL). The supernatant was collected on days 1, 4, and 7, centrifuged, and stored at −20° C. Cytokine (Interleukin 4, Interleukin 5, Interleukin 13, Interleukin 2, Interferon-γ, Interleukin 4, Interleukin 5, Interleukin 13, and Interleukin 17) levels were measured by multiplex ELISA (Enzyme Linked Immunosorbent Assay) for the samples collected on days 1, 4, and 7. Results based on 1 day (24 hours) of whole blood cell-based cytokine assay using staphylococcal enterotoxin B (SEB) stimulation were better predictive of asthma status as compared to tests based on longer durations and test based on other stimulants.

Results

The levels of a type 2 cytokines (Interleukin 4, Interleukin 5, and Interleukin 13), a type 1 cytokine (Interferon-γ), a T helper 17 cytokine (Interleukin 17), and Interleukin 2 that were produced and secreted by peripheral blood mononuclear cells and whole blood cells following a 24 hour incubation with a stimulant (e.g., Staphylococcal enterotoxin B (SEB)) were measured. Construct validity (the degree to which a test measures what it claims to be measuring) was assessed by determining the association between cytokine levels and asthma status and criterion validity (a degree of correlation of a test of interest with gold standard) was determined by analyzing correlation coefficients of cytokines secreted by peripheral blood mononuclear cells and whole blood cells.

Prediction of Asthma Status by Whole Blood Cell—Vs Peripheral Blood Mononuclear Cells-Based Cytokine Assays Construct validity for predicting asthma status was compared between whole blood cells- vs. peripheral blood mononuclear cells-based cytokine assays. The ratios of cytokines secreted by whole blood cells or peripheral blood mononuclear cells stimulated with staphylococcal enterotoxin B for 24 hours were measured and compared between individuals with asthma and those without asthma (controls). Overall, whole blood cell-based cytokine assays better predicted asthma status, compared to peripheral blood mononuclear cells-based cytokine assays. For example, three cytokine ratios (the Interferon-γ:Interleukin 4, Interleukin 4:Interleukin 2, and Interleukin 5:Interleukin 2 ratios) of whole blood cell-based assays and only one cytokine ratio (Interleukin 4:Interleukin 2 ratio) of peripheral blood mononuclear cells based assays predicted asthma status (p-value<0.05 in all) as summarized in Table 2.

TABLE 2

Associations of cytokine ratios with asthma status.

| 24 hour incubation with Staphylococcal Enterotoxin B | Sample source | Individuals without asthma[a] (n = 10) | Individuals with asthma[a] (n = 10) | P-value[b] |
|---|---|---|---|---|
| IFN-γ/IL-4 | Whole Blood | 3.77 (2.15, 3.98) | 1.90 (1.45, 3.24) | 0.017 |
| | PBMC | 3.63 (3.15, 3.84) | 3.32 (2.97, 3.65) | 0.30 |
| IL-4/IL-2 | Whole Blood | 0.27 (0.26, 0.28) | 0.43 (0.28, 0.56) | 0.004 |
| | PBMC | 0.26 (0.25, 0.27) | 0.27 (0.26, 0.28) | 0.03 |
| IL-5/IL-2 | Whole Blood | 0.56 (0.49, 0.58) | 0.63 (0.61, 0.72) | 0.002 |
| | PBMC | 0.53 (0.45, 0.61) | 0.60 (0.52, 0.64) | 0.34 |
| IFN-γ/IL-5 | Whole Blood | 1.86 (1.16, 2.01) | 1.31 (1.06, 1.50) | 0.21 |
| | PBMC | 1.67 (1.54, 2.03) | 1.53 (1.24, 1.63) | 0.09 |
| IFN-γ/IL-13 | Whole Blood | 1.43 (0.82, 1.51) | 1.24 (1.00, 1.33) | 0.28 |
| | PBMC | 1.38 (1.27, 1.49) | 1.24 (1.12, 1.46) | 0.28 |
| IFN-γ/IL-2 | Whole Blood | 0.98 (0.69, 1.08) | 0.82 (0.68, 1.03) | 0.68 |
| | PBMC | 0.93 (0.82, 0.98) | 0.89 (0.80, 0.97) | 0.62 |

TABLE 2-continued

Associations of cytokine ratios with asthma status.

| 24 hour incubation with Staphylococcal Enterotoxin B | Sample source | Individuals without asthma[a] (n = 10) | Individuals with asthma[a] (n = 10) | P-value[b] |
|---|---|---|---|---|
| IL-13/IL-2 | Whole Blood | 0.73 (0.69, 0.79) | 0.79 (0.56, 1.00) | 0.73 |
|  | PBMC | 0.65 (0.60, 0.71) | 0.70 (0.59, 0.75) | 0.47 |
| IL-17/IL-2 | Whole Blood | 0.54 (0.44, 0.61) | 0.58 (0.50, 0.68) | 0.38 |
|  | PBMC | 0.64 (0.62, 0.66) | 0.69 (0.57, 0.74) | 0.31 |

[a]Median (Interquartile range);
[b]Wilcoxon test

Correlation Between Whole Blood Cell Vs. Peripheral Blood Mononuclear Cells Based Cytokine Assays Whole blood and peripheral blood mononuclear cells cultures demonstrated moderate correlation for cytokine ratios, including Interleukin 5/Interleukin 2 (rho=0.40, p-value 0.08), Interleukin 13/Interleukin 2 (rho=0.44, p-value=0.05), and Interleukin 17/Interleukin 2 (rho=0.40, p-value 0.08), in response to Staphylococcal enterotoxin B (SEB) (Table 3). Whole blood cell-based Interleukin 5/Interleukin 2 ratios show criterion validity. While based on construct validity and criterion validity, whole blood cell-based Interleukin 5/Interleukin 2 ratio was a suitable measure for detecting the underlying type 2 immune response, other type 2 cytokine ratios such as Interleukin 4/Interleukin 2 also were suitable measures for detecting type 2 immune response as shown in the Table 2.

TABLE 3

Correlation of cytokine ratio between peripheral blood mononuclear cells and whole blood cells (Spearman's rho)*

| 24 hour incubation with SEB | Peripheral blood mononuclear cells (PBMC) | | | | | | | | |
|---|---|---|---|---|---|---|---|---|---|
| Whole blood | IFN-γ/ IL-4 | IFN-γ/ IL-5 | IFN-γ/ IL-13 | IFN-γ/ IL-2 | IL-4/ IL-2 | IL-5/ IL-2 | IL-13/ IL-2 | IL-17/ IL-2 | P-value** |
| IFN-γ/ IL-4 | 0.19 | 0.16 | 0.09 | 0.09 | −0.18 | −0.07 | −0.01 | −0.43 | 0.43 |
| IFN-γ/ IL-5 | 0.41 | 0.19 | 0.17 | 0.29 | −0.28 | 0.07 | 0.11 | −0.32 | 0.41 |
| IFN-γ/ IL-13 | 0.47 | 0.31 | 0.25 | 0.37 | −0.21 | −0.07 | −0.03 | −0.30 | 0.29 |
| IFN-γ/ IL-2 | 0.30 | 0.08 | 0.16 | 0.38 | 0.01 | 0.33 | 0.20 | −0.15 | 0.10 |
| IL-4/ IL-2 | −0.02 | −0.40 | −0.20 | 0.15 | 0.32 | 0.46 | 0.36 | 0.35 | 0.17 |
| IL-5/ IL-2 | −0.35 | −0.43 | −0.32 | −0.11 | 0.58 | 0.40 | 0.26 | 0.25 | 0.08 |
| IL-13/ IL-2 | −0.30 | −0.34 | −0.23 | −0.07 | 0.28 | 0.57 | 0.44 | 0.28 | 0.05 |
| IL-17/ IL-2 | −0.05 | 0.24 | 0.08 | 0.05 | 0.20 | 0.12 | 0.22 | 0.40 | 0.08 |

*Log-transformed data (eg, IL-5/IL-2 means a ratio of log-transformed [(IL-5) + 10] to log-transformed [(IL-2) + 10]
**P-value: : Statistical significance for correlation of the corresponding cytokine ratios between PBMC and whole blood in bold (e.g., the first p-value of 0.43 is for statistical significance of correlation between IFN-γ/IL-4 from PBMC and h IFN-γ/IL-4 from whole blood (e.g., correlation: 0.19))

Figure 1:
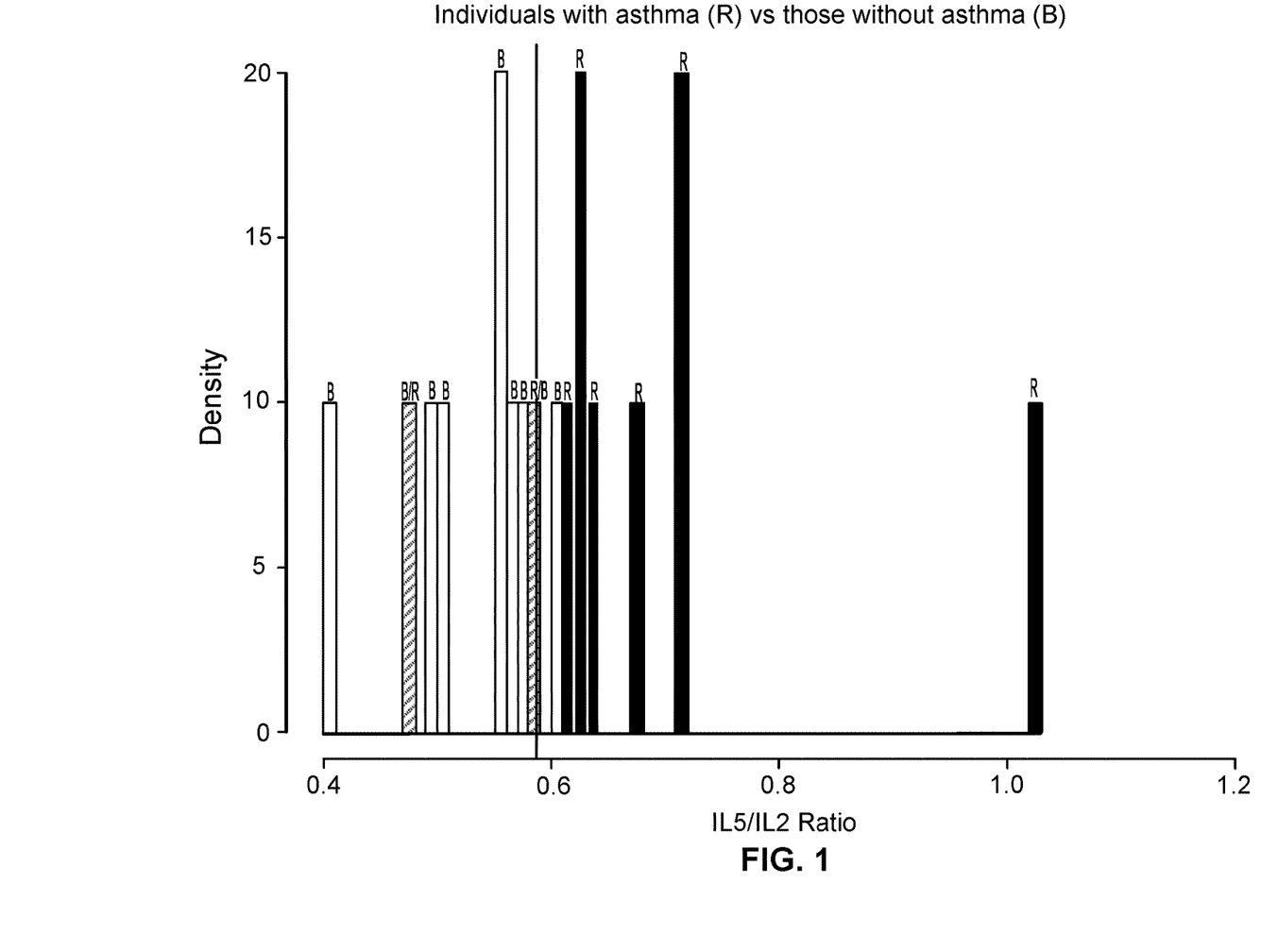
FIG. 1 is a graph showing a cut-off score for differentiating individuals with asthma from those without asthma based on Interleukin 5/Interleukin 2 ratio derived from cytokine secretion by whole blood after stimulation with Staphylococcal Enterotoxin B for 24 hours.

Identification of a Cut Off Score for Whole Blood Cell-Based Cytokine Assays in Differentiating Patients with Asthma from Healthy Individuals The ratio of Interleukin 5/Interleukin 2 after stimulating whole blood cells with staphylococcal enterotoxin B (SEB) for 24 hours was determined to provide an optimum cut off to predict asthma status (i.e., differentiate asthma patients from healthy individuals). For example, a cut-off score for the ratio of Interleukin 5/Interleukin 2 of 0.59 differentiates individual with asthma [mean (95% Confidence interval) for the ratio: 0.67 (0.57-0.77)] from individuals without asthma [mean (95% Confidence interval: 0.53 (0.49-0.58); p-value=0.002] as shown in FIG. 1. Based on this cut-off score, an area under the curve (which quantified the overall ability of a test to discriminate between those individuals with a disease and those without a disease of interest) was 0.91. The corresponding sensitivity was 0.9, and specificity was 0.9.

Similarly, a cut-off score for the ratio of Interleukin 4 to Interleukin 2 of 0.40 differentiated individuals with asthma [mean (95% Confidence interval) for the ratio: 0.47 (0.30-0.63)] from individuals without asthma [mean (95% Confidence interval: 0.27 (0.25-0.30); p-value=0.004]. Based on this cut-off score, an area under the curve was 0.89.

Figure 2:
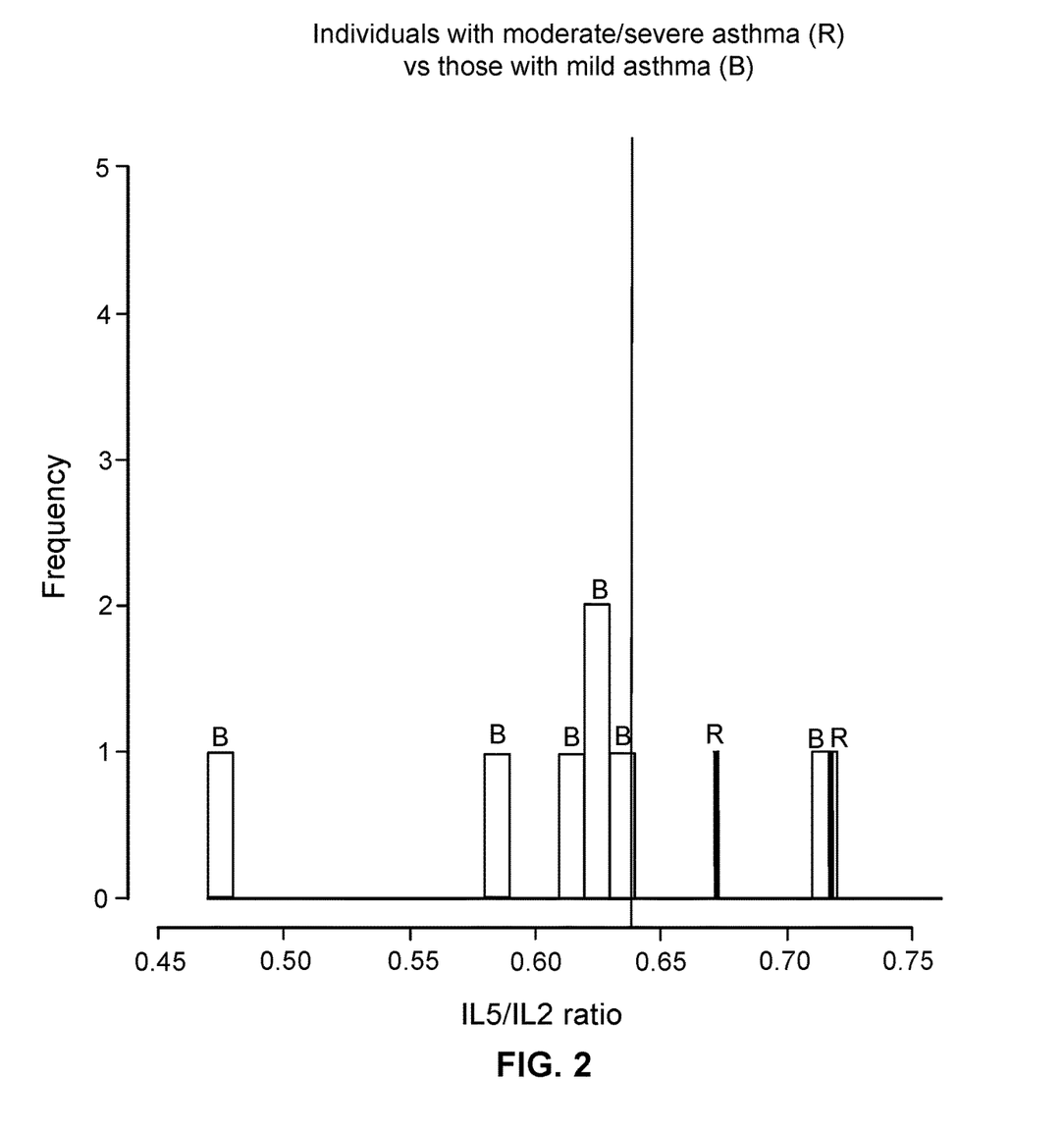
FIG. 2 is a graph showing a cut-off score for differentiating individuals with moderate or severe persistent asthma (defined by use of medium or high-dose inhaled corticosteroids) from those with mild persistent asthma (defined by use of low dose inhaled corticosteroids or no use) based on Interleukin 5/Interleukin 2 ratio derived from cytokine secretion by whole blood after stimulation with Staphylococcal Enterotoxin B for 24 hours.

Identification of a Cut Off Score for Differentiating Patients with Severe Asthma from Those with Mild Asthma To identify a cut off score, which differentiates individuals with moderate or severe persistent asthma (defined by medium/high dosage of daily inhaled corticosteroid use) from those with mild persistent asthma (defined by no or low dose inhaled corticosteroid use), a further exploratory analysis was performed. The cut off score for Interleukin 5/Interleukin 2 to differentiate moderate or severe asthma from mild asthma was 0.64 [mean (95% Confidence interval) of 0.69 (0.40-0.98) for individuals with moderate or severe asthma vs. 0.66 (0.53-0.80) for those with mild persistent asthma] as shown in FIG. 2. Based on this cut-off score, the area under the curve was 0.81. The corresponding sensitivity was 1.0, and specificity was 0.75.

Similarly, the cut off score for Interleukin 4/Interleukin 2 to differentiate moderate or severe asthma from mild asthma was 0.67 [mean (95% Confidence interval) of 0.53 (−1.2-2.2) for individuals with moderate or severe asthma vs. 0.45 (0.24-0.65) for those with mild persistent asthma]. Based on this cut-off score, the area under the curve was 0.69. The corresponding sensitivity was 0.5, and specificity was 0.88.

A replication study was performed using an independent sample of 17 subjects (i.e., replication cohort, Table 4) to reproduce the original study findings. In this replication study, the same study procedures were followed to assess the levels of type 2 cytokines (Interleukin 4 and Interleukin 5) and Interleukin 2 that were secreted by whole blood cells following a 24-hour incubation with a stimulant (e.g., Staphylococcal enterotoxin B, SEB).

TABLE 4

Baseline patient characteristics (a replication cohort).

| Characteristic | Individuals without asthma (n = 9) | Individuals with asthma (n = 8) | P-value |
|---|---|---|---|
| Age in years, median (IQR)* | 9.7 (8.9, 11.6) | 13.3 (6.1, 16.8) | 0.47 |
| Male gender, n (%) | 4 (50) | 5 (55) | 1.0 |
| Caucasian, n (%) | 6 (75) | 5 (55) | 0.61 |
| Allergic rhinitis, n (%) | 0 | 4 (44) | 0.08 |
| Atopic dermatitis, n (%) | 0 | 1 (11) | 1.00 |
| Total IgE, median (IQR)* | 35.9 (3.7, 107.5) | 53.7 (9.6, 160.3) | 0.53 |
| Atopic/sensitization status, n (%)** | 3 (37) | 6 (66) | 0.34 |

*Interquartile range;
**Determined by positive serum-specific (>35 kU/L) serum-specific IgE levels to cat dander, short ragweed, Timothy grass, Elm tree, Oak tree, house dust mite (*Dermatophagoides farina, Dermatophagoides pteronyssinus*), and *Alternaria Tenuis*.

Cut off scores for differentiating patients with asthma from healthy individuals were identified from the development cohort (i.e., 0.59 for Interleukin 5/Interleukin 2 and 0.40 for Interleukin 4/Interleukin 2). Table 5 summarized the association between asthma status and the cytokine ratio (i.e., Interleukin 5/Interleukin 2 and Interleukin 4/Interleukin 2) among the replication cohort. Table 6 showed positive predictive value and negative predictive value for the used cut off ratios given each cytokine ratio and cohort. The corresponding sensitivity and specificity for the replication cohort were 0.56 and 0.63 for Interleukin 5/Interleukin 2, and 0.44 and 1.0 for Interleukin 4/Interleukin 2. The area under the curve were 0.4 and 0.55 for Interleukin 5/Interleukin 2 and Interleukin 4/Interleukin 2, respectively.

TABLE 5

Associations of cytokine ratios with asthma status (replication cohort).

| 24 hour incubation with Staphylococcal Enterotoxin B | Sample source | Individuals without asthma[a] (n = 9) | Individuals with asthma[a] (n = 8) | P-value[b] |
|---|---|---|---|---|
| IL-5/IL-2 | Whole Blood | 0.54 (0.51, 0.67) | 0.60 (0.55, 0.66) | 0.41 |
| IL-4/IL-2 | Whole Blood | 0.34 (0.31, 0.36) | 0.38 (0.36, 0.43) | 0.014 |

[a]Median (Interquartile range);
[b]Wilcoxon test

TABLE 6

Performance of each ratio in discriminating asthma status using the same cut-off scores for the development and replication cohorts.

| | IL5/IL2 | | IL4/IL2 | |
|---|---|---|---|---|
| | Development cohort | Replication cohort | Development cohort | Replication cohort |
| Cut-off | 0.59 | 0.59 | 0.40 | 0.40 |
| PPV* | 0.79 | 0.39 | 1 | 1 |
| NPV** | 0.95 | 0.77 | 0.85 | 0.81 |

*PPV: positive predictive value;
**NPV: Negative predictive value

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a medical condition in a human, wherein said method comprises administering an anti-type 2 therapy to a human identified as having an Interleukin 4 to Interleukin 2 ratio in a whole blood cell based cytokine assay greater than 0.4, wherein the severity of said medical condition within said human is reduced.

2. The method of claim 1, wherein said medical condition is asthma.

3. The method of claim 1, wherein said anti-type 2 cytokine therapy is an anti-Interleukin 4 antibody therapy, an anti-Interleukin 5 antibody therapy, or an anti-Interleukin 13 antibody therapy.

* * * * *